United States Patent [19]
Berkeley

[11] 4,325,363
[45] Apr. 20, 1982

[54] POSTURE TRAINING THERAPEUTIC NECK SUPPORT

[76] Inventor: Joseph Berkeley, 1244 Devonshire Rd., Windsor, Ontario, Canada, N8X 1J3

[21] Appl. No.: 129,738
[22] Filed: Mar. 12, 1980

Related U.S. Application Data

[63] Continuation of Ser. No. 919,130, Jun. 26, 1978, abandoned.

[51] Int. Cl.³ .............................................. A61F 5/00
[52] U.S. Cl. ................................... 128/75; 128/76 R; 128/78; 128/DIG. 23
[58] Field of Search ............... 128/75, 76 R, 78, 87 B, 128/DIG. 23

[56] References Cited

U.S. PATENT DOCUMENTS

| | | | |
|---|---|---|---|
| 2,818,063 | 12/1957 | Smith et al. | 128/87 B |
| 3,285,243 | 11/1966 | Yellin | 128/75 |
| 3,343,532 | 9/1967 | Zumaglini | 128/75 |
| 3,477,425 | 11/1969 | Grassl | 128/75 |
| 3,504,667 | 4/1970 | McFarlane | 128/75 |
| 3,512,523 | 5/1970 | Barnett | 128/75 |
| 3,717,143 | 2/1973 | Johnson | 128/78 |
| 4,034,747 | 7/1977 | Leroy | 128/DIG. 23 |

Primary Examiner—Robert W. Michell
Assistant Examiner—Francis T. Jaworski
Attorney, Agent, or Firm—Chas. Krassov

[57] ABSTRACT

This invention consists of a collar which is worn as a neck support for posture training and therapeutic purposes. It is made of a soft spongy plastic material of a shape to fit the contour of the neck, and is reinforced around its rim with a narrow band of a stiff but flexible plastic material. The collar is provided with a plurality of spaced vertical stays which are made of longitudinal tubes containing removable strips of metal therein for controlling the shape and degree of stiffness of the collar. The spaces on the collar between the stays are open to provide ventilation. The collar is held around the neck by strips of adhesive tape such as "Velcro" which join the ends of the collar. Additional and variable support is provided by separate vertical supports which can be attached at various heights and locations on the collar, by "Velcro" type adhesive. These vertical supports are made of a double layer of soft spongy material with metal inserts therein for stiffness and by means of which these supports can be bent into required shapes.

2 Claims, 4 Drawing Figures

U.S. Patent
Apr. 20, 1982
4,325,363
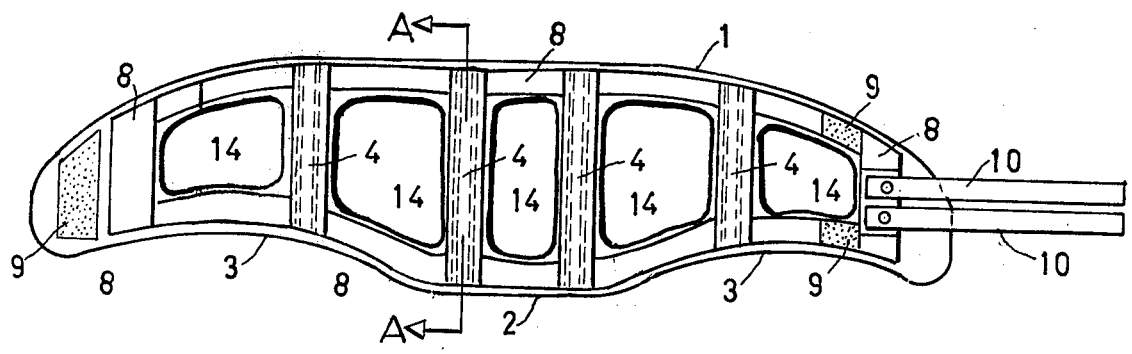
FIG.1
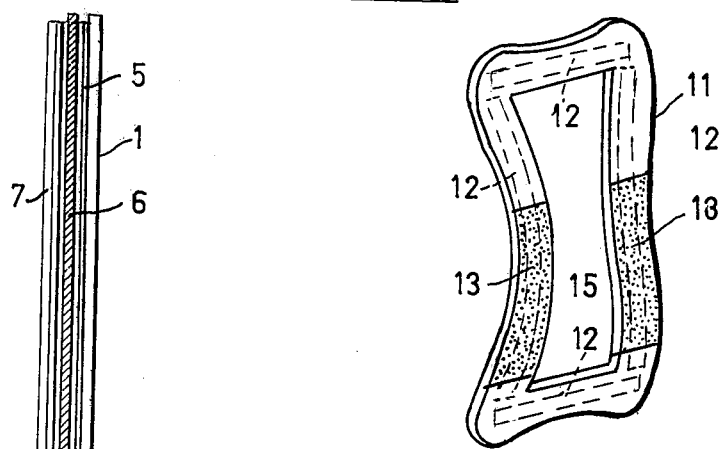
FIG.2
FIG.3
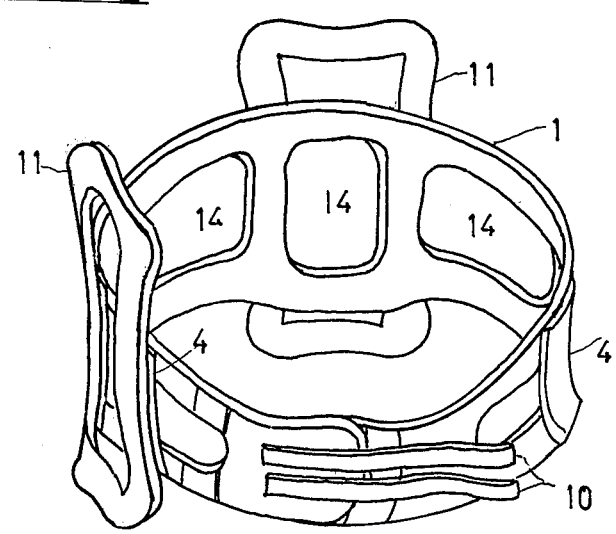
FIG.4

POSTURE TRAINING THERAPEUTIC NECK SUPPORT

This is a continuation of application Ser. No. 919,130 filed June 26, 1978, now abandoned.

This invention relates generally to neck supports which are worn by people for various reasons, and particularly to such supports which are prescribed by physicians for therapeutic purposes.

Generally, such supports, which are in the form of a collar worn around the neck, and which are beneficial to the person wearing one, nevertheless cause considerable discomfort during the various functions the body performs during the day; so that, by way of example, conditions which are tolerable during daylight functions, can become very disturbing during the night time sleeping period.

Another objection to the use of present day neck supports is the fact that they are designed for average conditions, and therefore cannot properly take care of an individual's variations in the front, back, length and contour of the neck, the neck joints, jaw movements, etc.

And yet another objection to the use of present day neck support collars is that their means of support is not variable and cannot provide the changes in the degree of stiffness and extent of support which may be required by the attending physician as the therapy progresses.

The object of this invention is therefore to provide a collar type of therapeutic neck support which overcomes the above objections, by providing a collar which is properly ventilated for additional comfort, which is equipped with means for adjusting its degree of stiffness, and which is provided with relocatable vertical supports, the heights, shapes, and locations of which can be adjusted to meet required conditions.

In describing the invention, reference will be made to the attached drawings in which, FIG. 1, is a view of the collar in an open position, FIG. 2, is section A—A of FIG. 1, FIG. 3, is a view of a vertical support, and FIG. 4, shows the collar in a closed position with one vertical support attached, by way of example.

The invention as shown in the drawings, consists of a collar which is worn around the neck, and which is made primarily of a background of thin sponge rubber or plastic material 1, on the inner side thereof which comes in contact with the skin of the neck. The collar is somewhat rounded on top; it has a widened area 2 in its center; one inwardly curved area 3 on each side of said widened area 2; and it terminates in narrowed down, rounded ends, in order to properly fit the countour of the back and front of the neck, and the shoulders. On its outer side, the collar is reinforced by being outlined with a narrow strip of a strong but flexible plastic 8, which is also thermolabile, around its rim. Thus, the therapist can, by applying heat to such plastic, form the collar into the shape most beneficial to the patient.

To give supporting stiffness vertically, to the collar, it is provided on its outside surface with spaced stays 4, and for ventilation purposes, in order to make the wearing of the collar more comfortable, the background of sponge material 1, is cut away as shown by the spaces 14.

The stays 4, a section of which is shown in FIG. 2, consists of a narrow tube 5 which runs the full height of the collar at the location where it is attached. The tube 5 has an insert therein of a thin metal strip 6, which can be removed from or reinserted into the tube 5 to reduce or increase the stiffness at any location on the collar. The metal strips 6 can also be bent to generally change the shape of the collar, as required.

On their outer surfaces the stay tubes 5 are provided with strips of an attachable and detachable adhesive 7, such as one known by the trademark "Velcro", to which various appendages can be attached or removed when required, as will be described further on in the specification.

In order to provide vertical support in addition to that supplied by the collar itself, in various locations around the neck and under the chin, a plurality of vertical supports 11, which are attachable to, removable from, and relocatable upon said collar, at various heights, as required. The support 11 as shown in FIG. 3, consists of an upright rectangle with rounded corners, slightly inwardly curved sides, and a cut away center 15. The supports 11 are made up of two layers of the same spongy material 1, as the background of the collar, and sandwitched between these layers are thin metal strips 12. Thus the supports 11 can be bent, shaped, and reused continuously as required. The supports 11 are also provided on one of their surfaces with "Velcro" type adhesives 13 by means of which they can be attached to the stays 4, or to companion adhesive pads 9 shown on the open collar in FIG. 1. A relative position between the collar and supports is shown in FIG. 4, and as many vertical supports can be arranged around the collar as required.

One end of the collar is provided with a pair of "Velcro" tapes 10,10, which adhere to one of the companion pads 9 on the other end, when the collar is closed, as shown in FIG. 4.

The many advantages in the use of this invention may be listed as follows:

(a) This neck support collar can be easily fitted on an unlimited variety of individuals.

(b) Support can be provided directly to the area or areas where it is mostly needed, or removed from such area where support is no further required.

(c) The degree of support such as stiffness, flexibility or immobilisation is easily adjustable, so that it can be easily converted from daylight to nighttime use, or changes required by changing stages in the treatment.

Many adjustments can be made by the person wearing the collar, by himself, acting upon prescribed instructions, and without the personal attendance of a therapist.

(e) The open areas in the collar provide a large degree of ventilation, thus reducing the usual discomfort which goes with the wearing of such collars.

Having described my invention, what I claim is:

1. A posture training and therapeutic neck support comprising a collar shaped to fit the front, back, and the upper and lower joints of the neck of a person, said collar being made of a soft, spongy material reinforced around the rim, a plurality of holes provided in the collar at intervals along a substantial portion of the length of the collar for ventilation, a plurality of generally vertical stays spaced at predetermined intervals between said holes along a substantial portion of the length of said collar, each of said stays comprising a narrow receptacle of a soft material and a thin strip of pliable material in at least some of said receptacles, which strips can be removed, shortened, and/or bent, as required, each of said narrow receptacles having attaching means extending substantially the length thereof, means for closing and opening the collar at the ends thereof, said collar also having attaching means near the ends thereof beyond the end ventilation holes therein, a plurality of separate, generally vertical supports of generally rectangular shape with the height exceeding the width and with the height exceeding the width of said collar for all portions of said collar, said supports having vertical legs and upper and lower legs connecting the vertical legs, with all of said legs enclosing thin bendable strips therein to enable said vertical supports to be bent and shaped as required, said supports having attachment means on the vertical legs thereof for temporarily attaching said vertical supports to said collar at said attaching means of said narrow receptacles to enable said supports to be moved to various heights relative to the width of said collar so as to project adjustable distances above the upper edge of said collar and to be located at various incremental positions along substantially the entire length of said collar, whereever additional support is required.

2. A posture training and therapeutic neck support comprising a collar having a shape to conform with the front, back, and the upper and lower joints of the neck of a person, said collar being made of soft, plastic material on the inside which comes in contact with the skin of the person, a strip of strong but pliable plastic material outlining the outside of the collar at the edges thereof to provide reinforcement, a plurality of open spaces spaced along said collar for ventilation purposes, said open spaces having generally vertical edges forming generally vertical webs between said spaces along said collar, a plurality of narrow tubes of soft material spaced at intervals along a substantial portion of the length of the collar on each of said webs and being generally vertical, at least some of said tubes containing thin strips of pliable metal which can be removed from the tubes, shortened, and/or bent, as required, a strip of "Velcro" located on the outside of each of said tubes on the outside of said collar and also being substantially vertically disposed, additional strips of "Velcro" at end portions of said collar near the end vertical edges of the end open spaces and also being on the outer surface of said collar, means for closing and opening the collar at the ends thereof, at least one separate vertical support which is generally rectangular in shape with an open central area, said support having vertical legs longer than the width of the collar and having upper and lower connecting legs, said vertical support being made of two layers of soft material with strips of thin, pliable, bendable material held between said layers of soft material to enable said vertical support to be shaped as required for a particular person, and pads of "Velcro" affixed to the vertical legs of said vertical support for attaching said vertical support to the "Velcro" strips mounted on the outside of said tubes on the outside of said collar and to the additional "Velcro" strips on the end portions of said collar, whereby said vertical support can be affixed to said collar at a plurality of positions along substantially the entire length of said collar and said vertical support can be moved vertically relative to said collar to adjust the extent to which said vertical support extends above the upper edge of said collar.

* * * * *